(12) United States Patent
Takeyama et al.

(10) Patent No.: US 7,043,153 B2
(45) Date of Patent: May 9, 2006

(54) IMAGE CAPTURING UNIT AND IMAGE CAPTURING DEVICE

(75) Inventors: Tetsuhide Takeyama, Tokyo (JP); Toshiyuki Nagaoka, Tokyo (JP)

(73) Assignee: Olympus Corporation, Tokyo (JP)

( * ) Notice: Subject to any disclaimer, the term of this patent is extended or adjusted under 35 U.S.C. 154(b) by 146 days.

(21) Appl. No.: 10/829,238

(22) Filed: Apr. 22, 2004

(65) Prior Publication Data

US 2004/0228003 A1 Nov. 18, 2004

(30) Foreign Application Priority Data

May 13, 2003 (JP) .......................... P2003-134440

(51) Int. Cl.
- *G03B 5/00* (2006.01)
- *G02B 1/06* (2006.01)
- *G02B 3/14* (2006.01)

(52) U.S. Cl. ...................... 396/72; 348/240.3; 359/666
(58) Field of Classification Search ................... 396/72; 348/240.3; 359/656, 666
See application file for complete search history.

(56) References Cited

U.S. PATENT DOCUMENTS

| 6,658,208 B1 * | 12/2003 | Watanabe et al. ............. 396/89 |
| 6,702,483 B1 * | 3/2004 | Tsuboi et al. ................ 396/449 |
| 6,806,988 B1 * | 10/2004 | Onuki et al. ................. 359/253 |
| 6,934,090 B1 * | 8/2005 | Nagaoka et al. ............. 359/665 |
| 2002/0176148 A1 | 11/2002 | Onuki et al. ................. 359/253 |

FOREIGN PATENT DOCUMENTS

| JP | 2001-249203 | 9/2001 |
| JP | 2001-249261 | 9/2001 |

OTHER PUBLICATIONS

Claude Gabay et al.: *Dynamic study of a Varioptic variable focal lens*, Proceedings of SPIE, vol. 4767 (2002).

* cited by examiner

*Primary Examiner*—W. B. Perkey
(74) *Attorney, Agent, or Firm*—Kenyon & Kenyon LLP

(57) ABSTRACT

An image capturing unit comprises a variable optical element, an optical unit, and a light-flux limiting section. The variable optical element includes a first liquid member, a second liquid member, and a container which contains the first liquid member and the second liquid member. An interfacial shape between the first liquid member and the second liquid member varies according to a voltage which is applied to the liquid members. The light-influx limiting section satisfies following condition $$0.1 < (\Phi - 2 \times h) < 20.0$$

where $\Phi$ (mm) indicates a maximum diameter for an axial light-flux in the variable optical element and h (mm) indicates a highest position of the axial light-flux on the light-incident end of the variable optical element. By doing this, it is possible to restrict a flare light and a ghost light and prevent impurities in the liquid members from being observed in the captured image.

12 Claims, 7 Drawing Sheets

IMAGE CAPTURING UNIT AND IMAGE CAPTURING DEVICE

INCORPORATED BY REFERENCE

The present application is based on patent application No. 2003-134440 filed May 13, 2003 in Japan, the content of which is incorporated herein by reference.

BACKGROUND OF THE INVENTION

1. Field of the Invention

The present invention relates to an image capturing unit which includes an optical element which makes use of electrocapillarity and an image capturing device.

2. Description of Related Art

In a conventional image capturing device such as a video-camera, some optical system can change a focal length. Most of these optical system change the focal length by moving a part of lenses or a part of lens group mechanically. Also, there has been invented a variable focal-length lens which can change the focal length by varying an optical characteristics in the lens. For example, there is a variable optical element which makes use of electrocapillarity.

Such a variable optical element is commonly known which is provided with a container for containing a first liquid member and a second liquid member which does not mix in the first liquid member. Also, such a variable optical element is provided with a first ring electrode which surrounds the first liquid member and a second ring electrode which surrounds the second liquid member. Here, an interfacial shape between the first liquid member and the second liquid member is varied according to a voltage which is applied to the liquid members (see "Robert E. Fischer, Current Developments in Lens Design and Optical Engineering III, U.S.A., SPIE, July 2000"). Also, various optical systems which are provided with such a variable optical element have been proposed (see page 16, FIG. 6 in Japanese Unexamined Patent Application, First Publication No. 2001-249203, and page 16 and FIG. 7 in Japanese Unexamined Patent Application, First Publication No. 2001-249261).

SUMMARY OF THE INVENTION

An image capturing unit of the present invention comprises a variable optical element, an optical unit which is disposed on a light-incident end of the variable optical element, and a light-flux limiting section. In this aspect of the present invention, it is preferable that the variable optical element includes a first liquid member, a second liquid member which does not mix in the first liquid member, and a container which contains the first liquid member and the second liquid member, an interfacial shape between the first liquid member and the second liquid member varies according to a voltage which is applied to the liquid members, and the light-influx limiting section satisfies a following condition (1);

$$0.1 < (\Phi - 2 \times h) < 20.0 \quad (1)$$

where $\Phi$ (mm) indicates a maximum diameter for an axial light-flux in the variable optical element and h (mm) indicates a highest position of the axial light-flux on the light-incident end of the variable optical element.

An image capturing unit of the present invention comprises a variable optical element, and an optical unit which is disposed on a light-incident end of the variable optical element. In this aspect of the present invention, it is preferable that the variable optical elements comprises a first liquid member, a second liquid member which does not mix in the first liquid member, a container which contains the first liquid member and the second liquid member, and an aperture member having aperture sections on both end in which diameters in the aperture sections are different, the aperture section having a small diameter in the aperture member is disposed near the light-incident end, an interfacial shape between the first liquid member and the second liquid member varies according to a voltage which is applied to the liquid members; and satisfies following conditions (2) and (3);

$$0.1 < (\Phi_1 - 2 \times h_1) < 20.0 \quad (2)$$

$$0.1 < (\Phi_2 - 2 \times h_2) < 20.0 \quad (3)$$

where $\Phi_1$ (mm) indicates a diameter for a small aperture section in the aperture member, $\Phi_2$ (mm) indicates a diameter for a large aperture section in the aperture member, $h_1$ (mm) indicates a highest position of the axial light-flux on the light-incident end of the variable optical element, and $h_2$ (mm) indicates a highest position of the axial light-flux on the interface between the first liquid member and the second liquid member.

In an image capturing unit of the present invention, it is preferable that the light flux limiting section serves for a cover glass which forms the container, and the light-incident surface serves for the interface between the cover glass and the first liquid member.

A mobile phone of the present invention comprises the image capturing unit of the present invention, a displaying section, an inputting button section, a voice inputting-outputting section, and an antenna.

DETAILED DESCRIPTION OF THE INVENTION

Figure 1A:
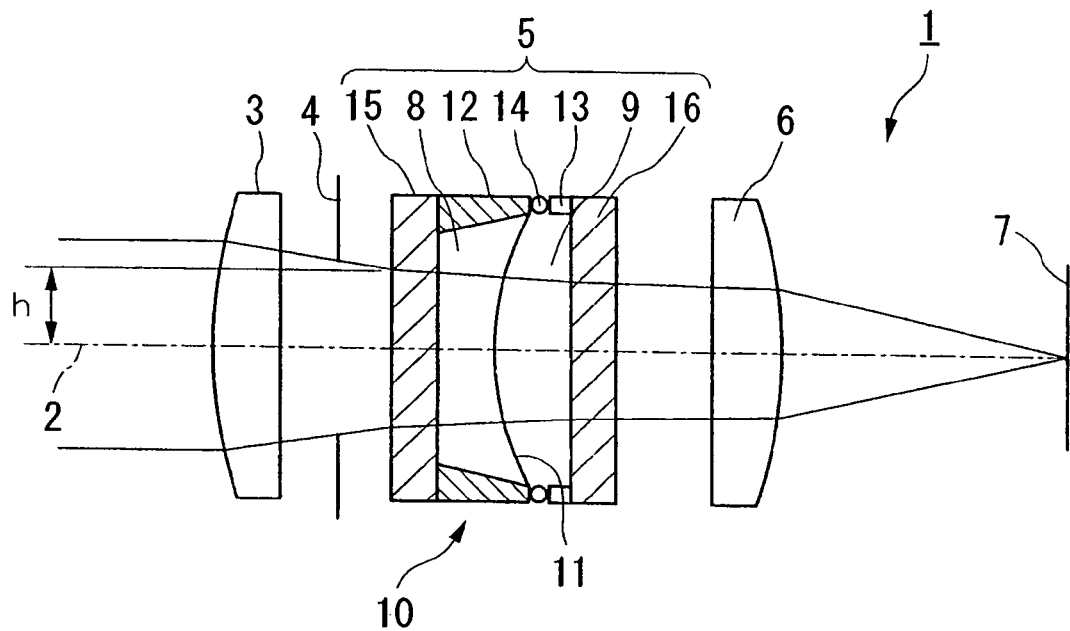
FIGS. 1A and 1B are views for showing a general structure of a first embodiment of the present invention.

An image capturing unit of the present invention comprises a variable optical element, an optical unit which is disposed on a light-incident end of the variable optical element, and a light-flux limiting section. In this aspect of the present invention, it is preferable that the variable optical element includes a first liquid member, a second liquid member which does not mix in the first liquid member, and a container which contains the first liquid member and the second liquid member, an interfacial shape between the first liquid member and the second liquid member varies according to a voltage which is applied to the liquid members, and the light-influx limiting section satisfies a following condition (1)

$$0.1<(\Phi-2\times h)<20.0 \tag{1}$$

where $\Phi$ (mm) indicates a maximum diameter for an axial light-flux in the variable optical element and h (mm) indicates a highest position of the axial light-flux on the light-incident end of the variable optical element.

It is preferable that an image capturing unit comprises an image capturing element, and a power supplying section, and the power supplying section commonly serves for capturing an image and varying optical characteristics.

It is preferable that a refractive index in the first liquid member is different from a refractive index in the second liquid member.

An image capturing unit comprises a variable optical element, and an optical unit which is disposed on a light-incident end of the variable optical element. In this aspect, it is preferable that the variable optical elements comprises a first liquid member, a second liquid member which does not mix in the first liquid member, a container which contains the first liquid member and the second liquid member, and an aperture member having aperture sections on both end in which diameters in the aperture sections are different, the aperture section having a small diameter in the aperture member is disposed near the light-incident end, an interfacial shape between the first liquid member and the second liquid member varies according to a voltage which is applied to the liquid members, satisfies following conditions (2) and (3)

$$0.1<(\Phi_1-2\times h_1)<20.0 \tag{2},$$

$$0.1<(\Phi_2 2\times h_2)<20.0 \tag{3}$$

where $\Phi_1$ (mm) indicates a diameter for a small aperture section in the aperture member, $\Phi_2$ (mm) indicates a diameter for a large aperture section in the aperture member, $h_1$ (mm) indicates a highest position of the axial light-flux on the light-incident end of the variable optical element, and $h_2$ (mm) indicates a highest position of the axial light-flux on the interface between the first liquid member and the second liquid member.

It is preferable that an image capturing unit comprises a variable optical element and a light-flux limiting section such that the variable optical element includes a first liquid member, a second liquid member which does not mix in the first liquid member, and a container which contains the first liquid member and the second liquid member, an interfacial shape between the first liquid member and the second liquid member varies according to a voltage which is applied to the liquid members, and the light-influx limiting section satisfies a following condition (4)

$$0.5<S<20.0 \tag{4}$$

where S (mm$^2$) indicates an area for a light flux having a maximum perspective on the light-incident end of the variable optical element.

It is preferable that the light flux limiting section serves for a cover glass which forms the container, and the light-incident surface serves for the interface between the cover glass and the first liquid member.

It is preferable that an image capturing unit comprises a variable optical element, and an image capturing element such that the variable optical element includes a first liquid member, a second liquid member which does not mix in the first liquid member, and a container which contains the first liquid member and the second liquid member, an interfacial shape between the first liquid member and the second liquid member varies according to a voltage which is applied to the liquid members, an absolute value for $R_{12}$-d is in a range between 10% and 500% of a length d (mm), where $R_{12}$ indicates a diameter of a curvature of the interface, and d indicates an optical path length of an axial principal light between the interface and a surface of the image capturing element.

It is preferable that the image capturing element is disposed on a light-emitting end of the variable optical element.

It is preferable that an image capturing device should be provided with the image capturing unit of the present invention.

It is preferable that a mobile phone of the present invention comprises the image capturing unit of the present invention, a displaying section, an inputting button section, a voice inputting-outputting section, and an antenna.

It is preferable that, an information terminal comprises the image capturing unit of the present invention, a displaying section, and a keyboard.

It is preferable that an endoscope device comprises the image capturing unit of the present invention, a light source, a signal processing circuit, and a power supply section.

Hereinafter, an embodiment of an image capturing unit is explained below with reference to FIG. 1A to FIG. 4.

Figure 1B:
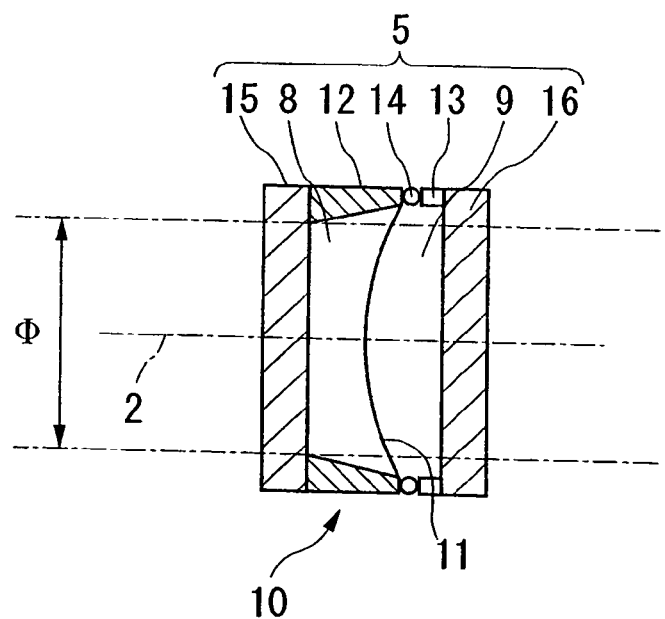

An image capturing unit 1 according to a first embodiment is shown in FIGS. 1A and 1B. The image capturing unit 1 comprises a first lens 3, an aperture 4 (a light flux limiting section), a variable optical element 5, a second lens 6, and an image capturing element 7 such that these members are disposed along an optical axis 2 so as to have certain intervals thereamong.

The variable optical element 5 comprises a first liquid member 8, a second liquid member 9 which does not mix in the first liquid member 8, and a container 10 for containing the first liquid member 8 and the second liquid member 9. Here, the first liquid member 8 and the second liquid member 9 do not mix with each other; therefore, an interface 11 is formed between the first liquid member 8 and the second liquid member 9. That is, there is a tendency that both the first liquid member 8 and the second liquid member 9 are separated with each other at a boarder such as the interface 11 in a closed space.

Furthermore, the container 10 comprises a first ring electrode 12, a second ring electrode 13, an insulating member 14, a first cover glass 15, and a second cover glass 16. The first ring electrode 12 having a hollow space thereinside is disposed so as to surround the first liquid member 8 such that a diameter of an inner surface of the first ring electrode 12 expands gradually toward an emitting direction of a light flux. Also, the second ring electrode 13 having a hollow space thereinside is disposed so as to surround the second liquid member 9.

Also, the insulating member 14 is disposed between the first ring electrode 12 and the second ring electrode 13 so as to insulate the electrodes from each other. Also, the first cover glass 15 is disposed near the first liquid member 8. The second cover glass 16 is disposed near the second liquid member 9.

Here, an interfacial shape of the interface 11 varies according to a voltage which is applied between the first ring electrode 12 and the second ring electrode 13; thus, the focal length of the variable optical element 5 varies accordingly.

A parallel light flux is incident into the image capturing unit 1 from the first lens 3. This light flux is an axial light flux. In such a case, the parallel light flux is converted to a converging light flux by the first lens 3. The converging light flux transmits through the aperture 4. In FIG. 1A, only a light flux which transmits through an aperture section in the aperture 4 is shown.

The light flux which transmits through the aperture 4 is incident into the variable optical element 5. After transmitting through the first cover glass 15, first liquid member 8, second liquid member 9, and the second cover glass 16, the light flux emanates from thereoutside. Consequently, the converging light flux which is emanated from the variable optical element 5 transmits through the second lens 6 so as to be condensed on the image capturing element 7.

In such a structure, the image capturing unit 1 is provided with a light flux limiting section which satisfies a following condition (1)

$$0.1<(\Phi-2\times h)<20.0. \quad (1)$$

Parameters $\Phi$ and h are explained. In a structure shown in FIG. 1A, the first lens 3 and the aperture 4 are disposed near the light-incident surface of the variable optical element 5. A parameter h (mm) serves for such a structure for indicating a highest height of the axial light flux on an incident surface of the variable optical element 5. Here, a portion of the light flux of which area is greater than the aperture section of the aperture 4 is blocked by the aperture 4. Therefore, the aperture 4 serves as a light flux limiting section.

The light flux is incident to a surface near the aperture 4 among two surfaces on the first cover glass 15. Here, if the first cover glass 15 is a thin member, there is not a big difference for the highest height of the light flux between two surfaces of the first cover glass 15. Therefore, it should be understood that the h (mm) may indicate the highest height of the axial light flux on a surface nearer to the first liquid member 8 among two surfaces of the first cover glass 15. Also, under such a condition, it should be noted that the first cover glass 15 contacts the first liquid member 8, and an end surface of the first ring electrode 12 which has two surfaces contacts the first cover glass 15.

On the other hand, as shown in FIG. 1B, it should be noted that nothing is disposed on a light-incident surface of the variable optical element 5. A parameter such as $\Phi$ serves for such a structure so as to indicate a minimum diameter of the axial light flux on the variable optical element 5. Here, the light flux which is incident into an entire surface of the first ring electrode 12 is blocked by an end surface of the first ring electrode 12 having two end surfaces which is disposed nearer to the first cover glass 15. Therefore, such an end surface serves as a light flux limiting section under condition that only a piece of variable optical element is used.

The minimum diameter of the axial light flux depends on the above end surface (an end surface of the first cover glass 15 in the first ring electrode 12). Therefore, it should be understood that a parameter $\Phi$ (mm) may indicate an inner diameter of the first ring electrode 12 on an end surface of the first cover glass 15. It is observed that the inner diameter of the first ring electrode 12 may be minimum on the first cover glass 15. Therefore, it is possible to understand that the $\Phi$ (mm) may indicate the minimum inner diameter of the first ring electrode 12. Also, it should be noted that the first cover glass 15 contact the first liquid member 8 under the above condition.

Here, for example, it is assumed that the first lens 3 and the aperture 4 are disposed such that a parameter h indicates 5.0 mm. Also, it is assumed that the first ring electrode 12 is disposed such that a parameter $\Phi$ indicates 13.0 mm. By doing this, the condition (1) indicates such that $\Phi-2\times h=3.0$ mm; thus, the condition (1) is satisfied.

In the image capturing unit 1 having the above structure, the light flux is incident into the first lens 3. By doing this, the incident light flux is condensed by the first lens 3. Consequently, the diameter of the light flux which is incident into the variable optical element 5 is restricted by the aperture 4 so as to be twice as high as the height h or lower. Consequently, the light flux is further condensed by the variable optical element 5 and the second lens 6 so as to be on the image capturing element 7. In such a case, it is possible to vary the shape of the interface 11 by adjusting the voltage which is applied between the first ring electrode 12 and the second ring electrode 13. By doing this, the light flux is focused on the image capturing element 7 by adjusting the focal length of the variable optical element 5.

In the above structure, an interval between the first ring electrode 12 and the incident light flux is 1.5 mm. Therefore, if the incident light flux is incident into the variable optical element 5, the incident light flux does not reach to the first ring electrode 12. Thus, a flare and a ghost image is restricted. As a result, it is possible to restrict a deterioration of image which is caused by such a flare and a ghost image.

Figure 2A:
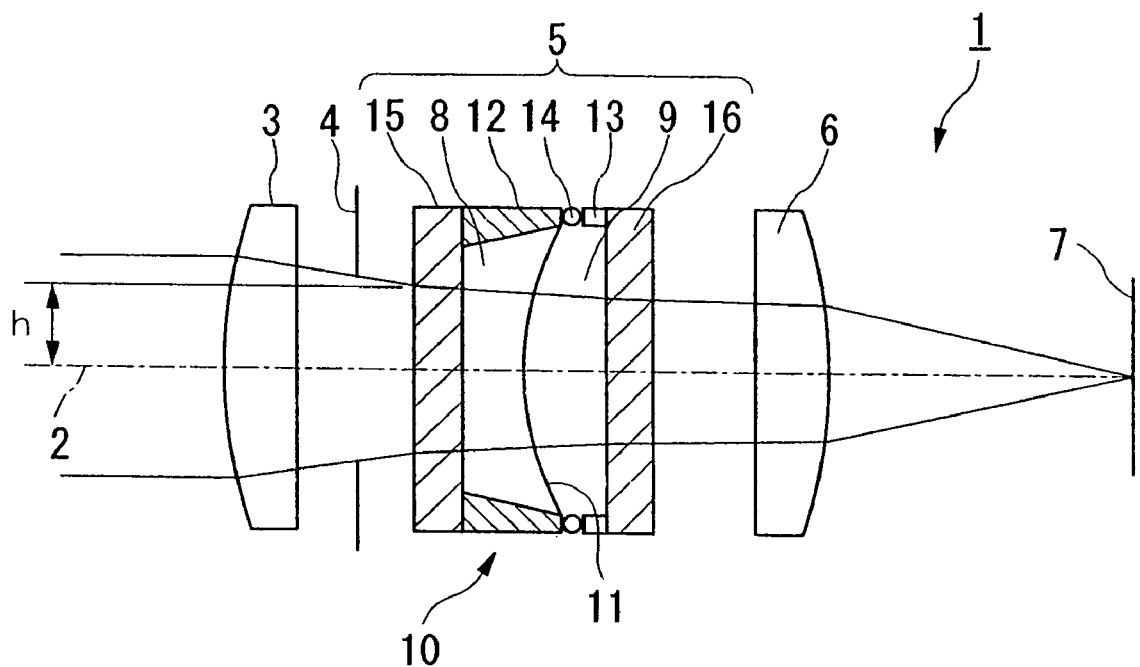
FIGS. 2A and 2B are views for showing a general structure of a second embodiment of the present invention.

Next, the image capturing unit 1 according to a second embodiment is explained below with reference to FIGS. 2A and 2B. Hereinafter, the same reference numerals are applied to corresponding members as shown in the first embodiment so as to omit the repeated explanation thereof.

In the present embodiment, the image capturing unit 1 is provided with a light flux limiting section which compatibly satisfies following conditions (2) and (3)

$$0.1<(\Phi_1-2\times h_1)<20.0 \quad (2)$$

$$0.1<(\Phi_2-2\times h_2)<20.0. \quad (3)$$

Here, parameters $\Phi_1$, $h_1$, $\Phi_2$, and $h_2$ are explained. In a structure shown in FIG. 2A, the first lens 3 and the aperture 4 are disposed near a light-incident surface of the variable optical element 5. Parameter $h_1$ (mm) and $h_2$ (mm) serves for such a structure. That is, $h_1$ indicates the highest height of the axial light flux on the light-incident surface of the variable optical element 5 similarly to a case of the first embodiment. Alternatively, $h_1$ (mm) indicates the highest height of the axial light flux on a surface of the first cover glass 15 having two surfaces nearer to the first liquid member 8. On the other hand, $h_2$ (mm) indicates the highest height of the axial light flux on the interface 11. Alternatively, $h_1$ (mm) indicates the highest height of the axial light flux on a surface of the first cover glass 15 having two surfaces nearer to the first liquid member 8. Here, the interface 11 is disposed to a surface of the first ring electrode 12 having two surfaces which is nearer to the second cover glass 16. Therefore, it is understood that the $h_2$ (mm) may indicate the highest height of the axial light flux which transmits the end surface of the first ring electrode 12 having two surfaces which is nearer to the second cover glass 16. Here, the axial light flux which is used for inducing $h_1$ and $h_2$ transmits through the aperture section of the aperture 4. As explained above, a portion of the light flux of which area is greater than the aperture section of the aperture 4 is blocked by the aperture 4. Therefore, the aperture 4 serves as a light flux limiting section.

Figure 2B:
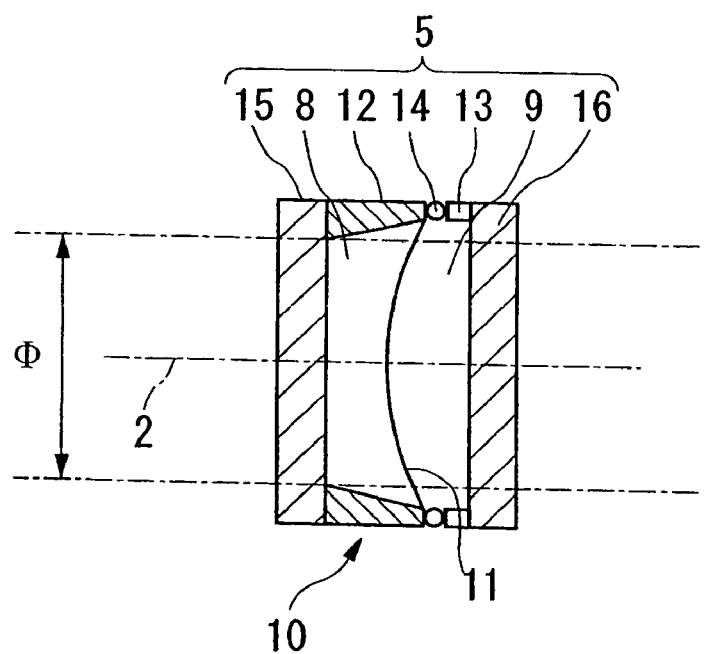

On the other hand, as shown in FIG. 2B, it should be noted that nothing is disposed on a light-incident surface of the variable optical element 5. A parameters $\Phi_1$ (mm) and $\Phi_2$ (mm) serve for such a structure. Here, the variable optical element 5 is provided with aperture member, on both side of which, aperture diameters are different. Furthermore, the aperture section is disposed such that a small aperture diameter should be disposed near the light-incident surface. The $\Phi_1$ (mm) indicates such a small aperture diameter. In the present embodiment, the first ring electrode 12 serves for such an aperture member. Therefore, it can be understood that $\Phi_1$ (mm) indicates an inner diameter of an end surface of the first ring electrode 12 having two end surfaces nearer to the first cover glass 15. On the other hand, $\Phi_2$ (mm) indicates a large aperture diameter of the aperture member. Therefore, it can be understood that $\Phi_2$ (mm) indicates an inner diameter of an end surface of the first ring electrode 12 having two end surfaces nearer to the second cover glass 16.

Here, the light flux which is incident into an entire surface of the cover glass 15 is blocked on an end surface of the first ring electrode 12 having two end surfaces nearer to the first cover glass 15. Therefore, such an end surface serves as a light flux limiting section if only a piece of variable optical element is used.

Here, for example, it is assumed that the first lens 3 and the aperture 4 are disposed such that a parameter $h_1$ indicates 4.5 mm and $h_2$ indicates 4.0 mm. Also, it is assumed that the first ring electrode 12 is disposed such that a parameter $\Phi 1$ indicates 10.0 mm and $\Phi 2$ indicates 11.0 mm. By doing this, $\Phi_1 - 2 \times h_1 = 2.0$ mm $\Phi_2 - 2 \times h_2 = 3.0$ mm. Thus, the conditions (2) and (3) are satisfied.

In the image capturing unit 1 having the above structure, similarly to a case of the first embodiment, the light flux is incident into the first lens 3. Accordingly, a diameter of the light flux which is incident into the variable optical element 5 by the aperture 4 is restricted to be as twice as high as the height $h_1$ or lower and twice as high as the height $h_2$ or lower. Consequently, the light flux is further condensed by the variable optical element 5 and the second lens 6 so as to be on the image capturing element 7. In such a case, a voltage which is applied between the first ring electrode 12 and the second ring electrode 13 is adjusted such that the incident light flux should be focused on the image capturing element 7.

According to the above structure, an interval between the first ring electrode 12 and the incident light flux is 1.0 mm near the first cover glass 15. Therefore, the incident light flux does not reach to the first ring electrode 12 even if the incident light flux is incident into the variable optical element 5. Therefore, a flare and a ghost image are restricted. Also, an interval between the first ring electrode 12 and the incident light flux is 1.5 mm near the second cover glass 16. Therefore, it is not necessary to form the variable optical element 5 in a large size. As a result, it is possible to restrict the deterioration of the image which is caused by the flare and the ghost image without increasing the size of the variable optical element 5.

Figure 3:
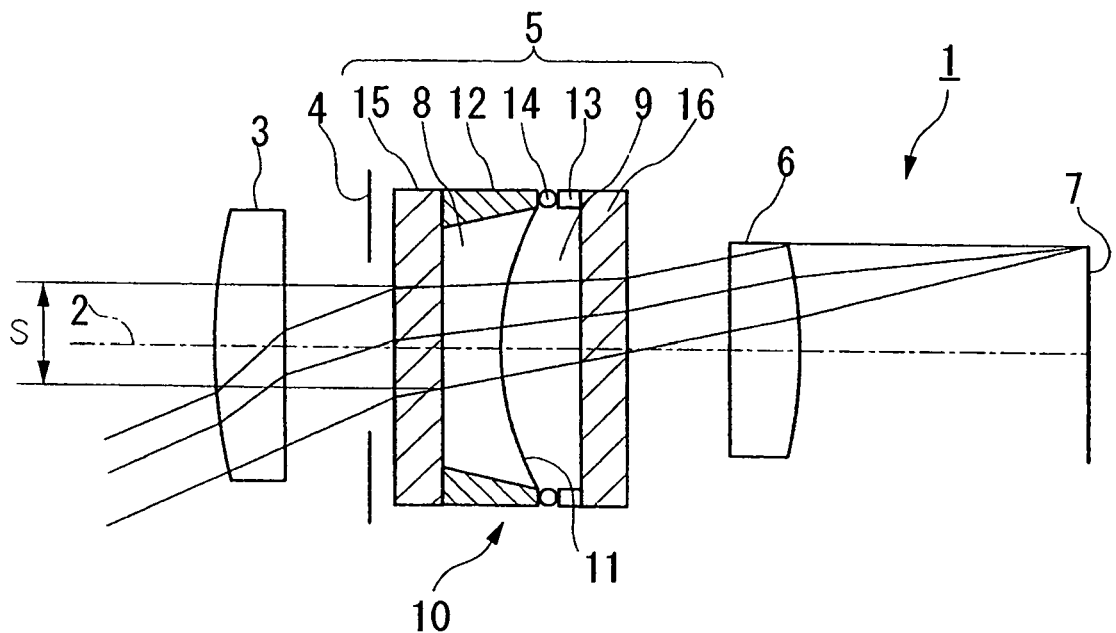
FIG. 3 is a view for showing a general structure of a third embodiment of the present invention.

Next, the image capturing unit 1 according to a third embodiment is explained below with reference to FIG. 3. Hereinafter, the same reference numerals are applied to corresponding members as shown in the first embodiment so as to omit the repeated explanation thereof.

In the present embodiment, the image capturing unit 1 is provided with a light flux limiting section which satisfies a following condition (4)

$$0.5 < S < 20.0 \tag{4}$$

where S (mm$^2$) indicates an area for a light flux having a maximum perspective on the light-incident end of the variable optical element.

Under the above condition, the light flux is incident in to an end surface of the first cover glass 15 having two end surfaces nearer to the aperture 4. Here, if the first cover glass 15 is a thin member, there is not a big difference for the highest height of the light flux between two surfaces of the first cover glass 15. Therefore, it is possible to understand that the above incident surface indicates a border surface between the first cover glass and the first liquid member.

Here, for example, the aperture 4 is disposed such that S (mm$^2$) is 2.0 mm$^2$. Accordingly, similarly to a case of the first embodiment, an area of the light flux which is incident into the first cover glass 15 is restricted so as to be less than an area S of the light flux under condition that a perspective angle is maximum by the aperture 4. In such a case, a voltage which is applied between the first ring electrode 12 and the second ring electrode 13 is adjusted such that the light flux is focused on the image capturing element 7.

According to the above structure, an area S of the light flux satisfies the condition (4); therefore, it is possible to prevent the impurities such as a dust in the first liquid member 8 and the second liquid member 9 from being captured in the image.

Figure 4:
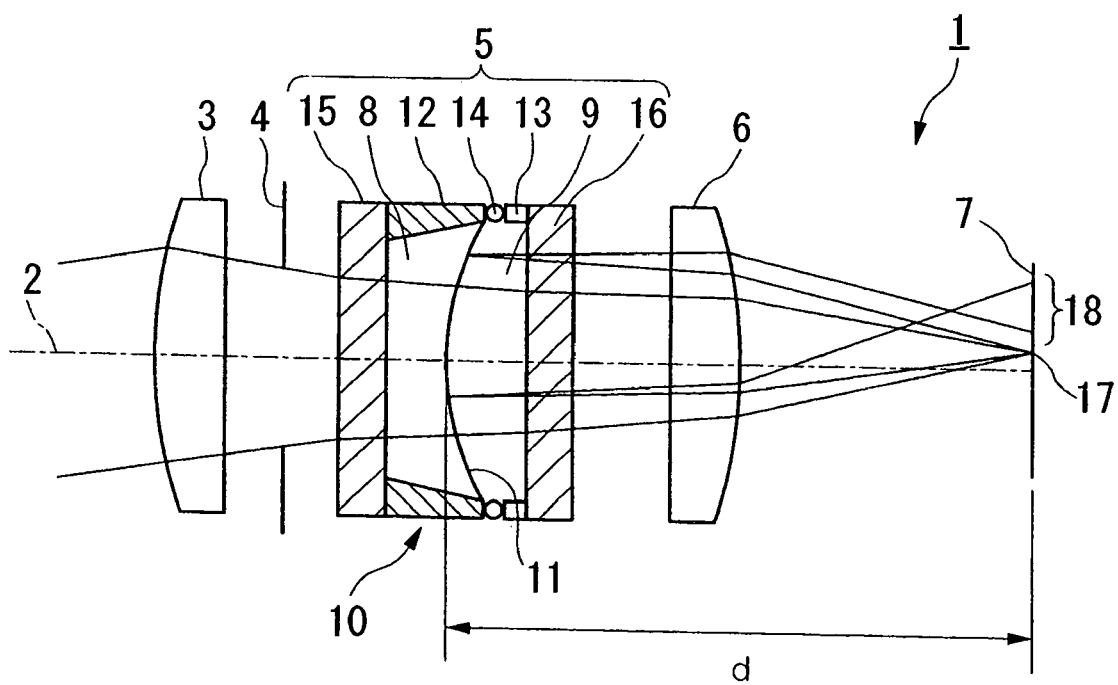
FIG. 4 is a view for showing a general structure of a fourth embodiment of the present invention.

Next, the image capturing unit 1 according to a fourth embodiment is explained below with reference to FIG. 4. Hereinafter, the same reference numerals are applied to corresponding members as shown in the first embodiment so as to omit the repeated explanation thereof. Reference numeral 17 indicates a proper focusing spot for the incident light flux into the optical system. Also, reference numeral 18 indicates a spot image which is caused by a ghost light from the interface 11.

In the image capturing unit 1, $R_{12}$ and d are set such that an absolute value for $R_{12}$-d is in a range between 10% and 500% of a length d (mm), where $R_{12}$ indicates a diameter of a curvature of the interface, and d indicates an optical path length of an axial principal light between the interface 11 and a surface of the image capturing element. Here, $R_{12}$ is set to be, for example, 23.0 mm. Also, d is set to be, for example, 20.0 mm.

In the image capturing unit 1 according to the above structure, similarly to a case of the first embodiment, a voltage which is applied between the first ring electrode 12 and the second ring electrode 13 is adjusted such that the incident light flux should be focused on the image capturing element 7.

According to the above structure, a ghost light which is caused by a reflection on the interface 11 is not focused in a small spot on the image capturing element 7. As a result, an optical energy of the ghost light which is caused by a reflection on the interface 11 may be reduced on each pixel on the image capturing element 7. Therefore, undesirable influence which may deteriorate the image quality can be restricted.

Here, it is preferable that the absolute value for $R_{12}$-d is in a range between 10% and 100% of a length d. Furthermore, it is preferable that the absolute value for $R_{12}$-d is in a range between 10% and 50% of a length d.

Here, it is possible to form the first cover glass 15 and the second cover glass 16 in various surfaces such as a spherical surface, an aspherical surface, a refractive optical surface, and a free-form surface.

Hereinafter, an image capturing device in which the image capturing unit 1 is used is explained specifically.

Figure 5:
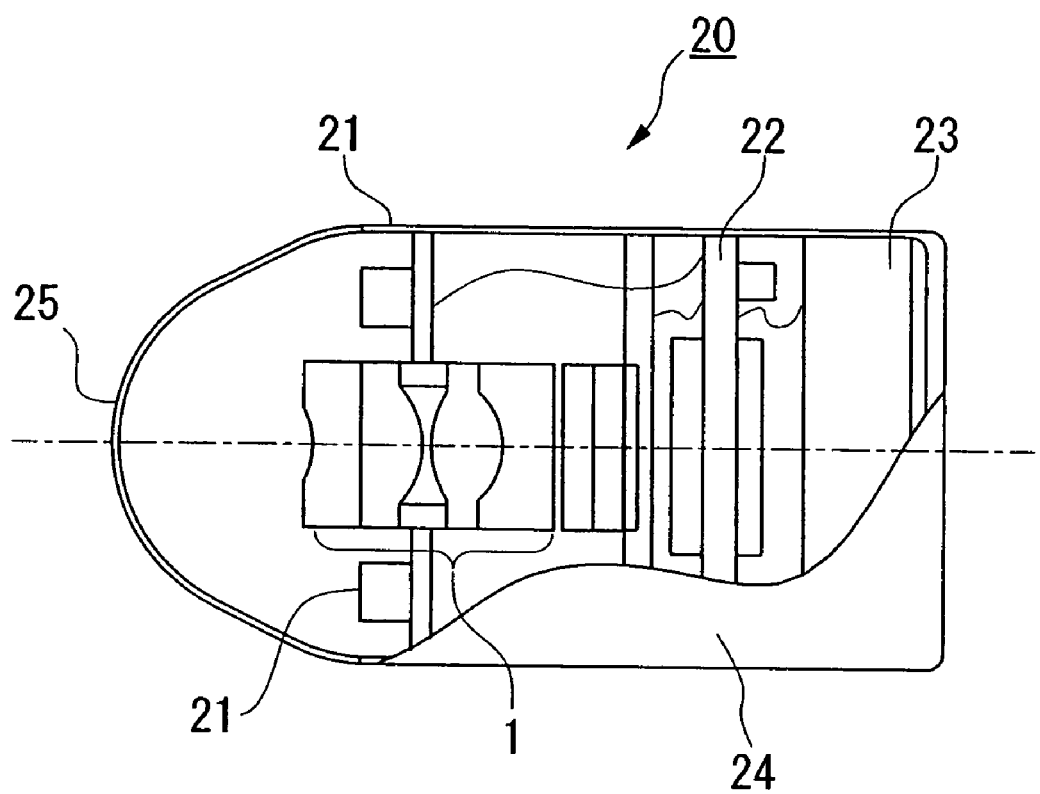
FIG. 5 is a cross section for showing a general structure of a capsule endoscope in which an image capturing unit is used.

In FIG. 5, an example for the image capturing unit 1 which is used for a capsule endoscope 20 is shown.

The capsule endoscope 20 comprises a light source 21, an image capturing unit 1, an image processing circuit 22 which processes a signal which is sent from the image capturing unit 1, and a battery 23 such that the above members are entirely covered by a cover 24.

A transparent window 25 is disposed on a tip of the cover 24. A light is projected via the transparent window 25. Also, the image capturing unit 1 receives a reflected light via the transparent window 25.

Figure 6A:
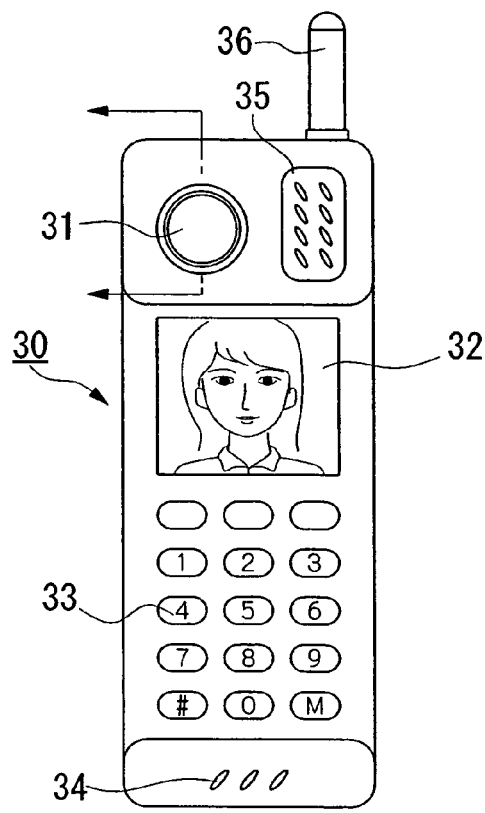
FIG. 6A is a front view for showing a general structure of a mobile terminal in which an image capturing unit is used.
Figure 6B:
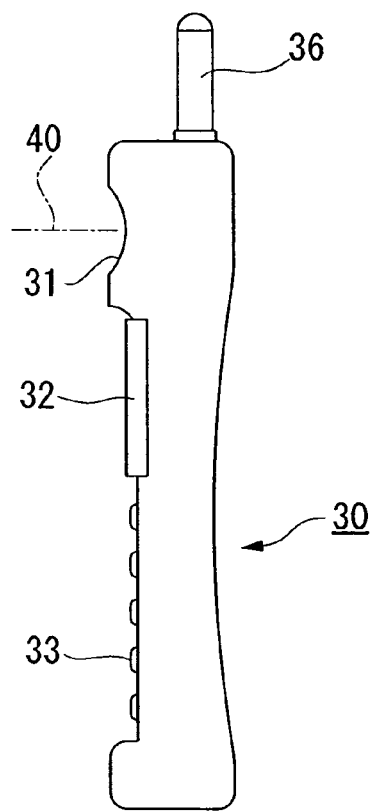
FIG. 6B is a side view therefor.
Figure 6C:
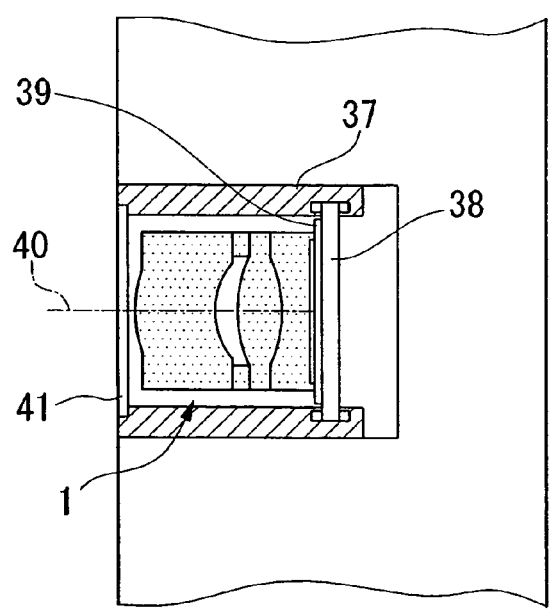
FIG. 6C is a cross section therefor.

Next, an example of the image capturing unit 1 whic is used for a mobile terminal 30 is shown in FIGS. 6A to 6C.

FIG. 6A is a front view. FIG. 6B is a side view. FIG. 6C is a cross section viewed in a line X—X in FIG. 6A.

The mobile terminal 30 comprises an image capturing section 31, in which a image capturing unit 1 is used, a monitoring section 32, an inputting section 33 for inputting a letter code and a command signal by using buttons and a dialing member, a microphone section 34, a speaker section 35, and an antenna 36 for transmitting and receiving in a wireless communication manner.

As shown in FIG. 6C, a CCD 39 which is included in the image capturing unit 1 is fixed so as to be electrically connected onto a circuit base board 38 which is fixed on a base board mounting section 37 in the mobile terminal 30. Also, in the mobile terminal 30, a cover glass 41 is disposed in a direction of an optical axis of an image capturing section 40 so as to be sealed thereinside.

Figure 7:
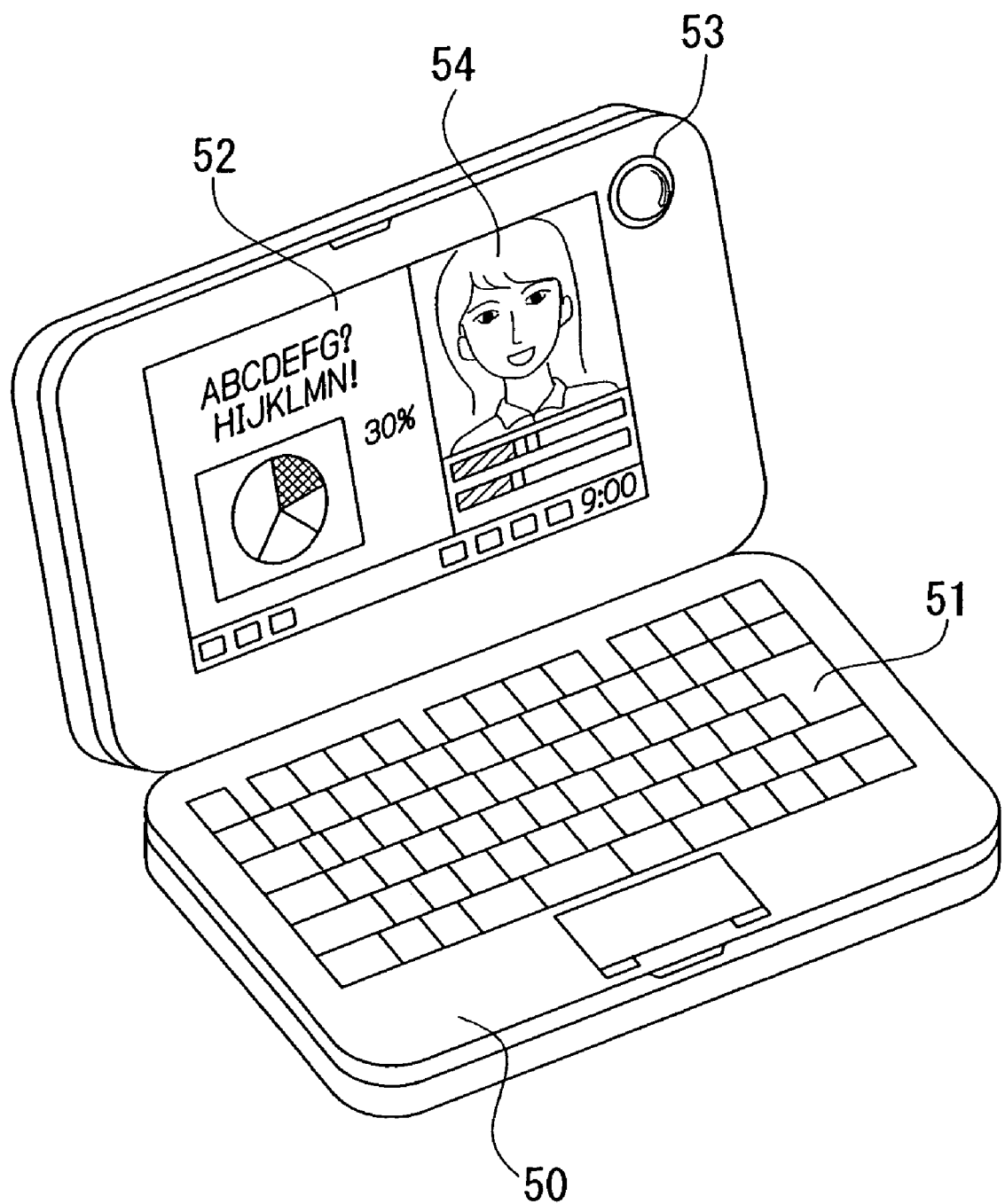
FIG. 7 is an isometric view for showing a general structure for a personal computer in which an image capturing unit is used.

Next, an example for a personal computer 50 in which the image capturing unit 1 is used is shown in FIG. 7. FIG. 7 is an isometric view for a general structure of the personal computer 50.

The personal computer 50 comprises a keyboard 51, a monitoring section 52, and an image capturing section 53. The monitoring section 52 can display an image 54 which includes an image which is captured by the image capturing section 53. The image capturing section 53 is disposed next to the monitoring section 52. The image capturing unit 1 (not shown in the drawing) is disposed inside the image capturing section 53 such that a cross section in the optical axis direction is the same as the cross section shown in FIG. 6C.

Figure 8:
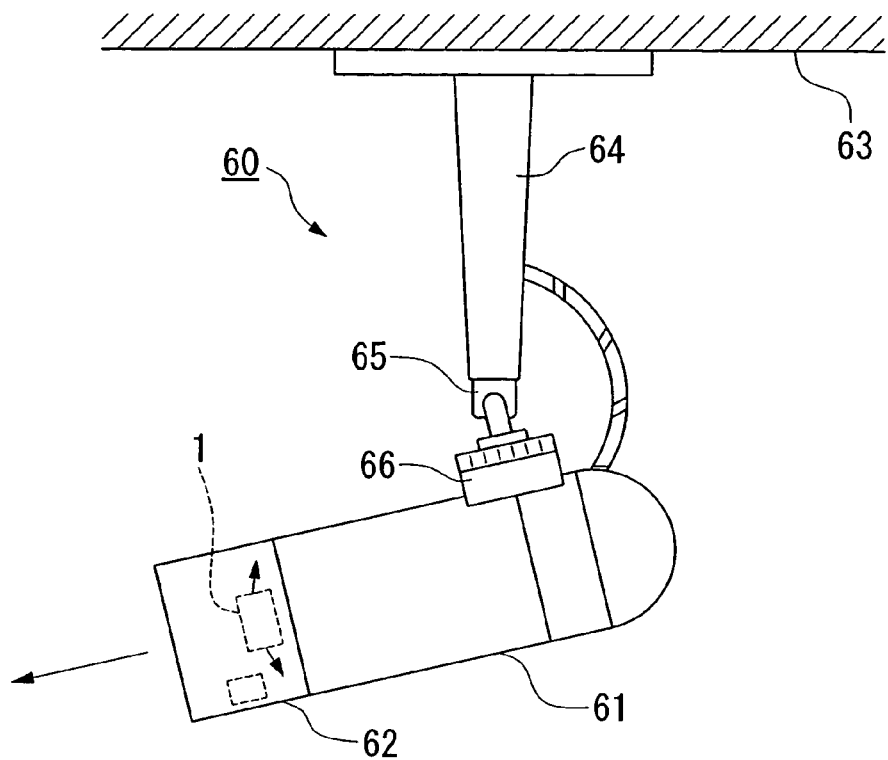
FIG. 8 is a side view for showing a general structure of a monitoring camera in which an image capturing unit is used.

Next, an example for a monitoring camera 60 in which the image capturing unit 1 is used is shown in FIG. 8. FIG. 8 is a side view for explaining a general structure of the monitoring camera 60.

The monitoring camera 60 comprises a circuit section 61 which forms a main body for the monitoring camera and an image capturing section 62. The monitoring camera 60 is attached to a mounting section 64 which is fixed on a ceiling 63 via a shaft 65 and a motor 66. The image capturing unit 1 is disposed inside the image capturing section 62 so as to monitor in a direction which is indicated by an arrow in FIG. 8. The image capturing unit 1 has the same cross section in the optical axis direction as the cross section which is shown in FIG. 6C so as to be fixed in the image capturing section 62. It is acceptable if the base board mounting section 37 shown in FIG. 6C is attached so as to freely swing by a rotating structure (not shown in the drawing).

Figure 9:
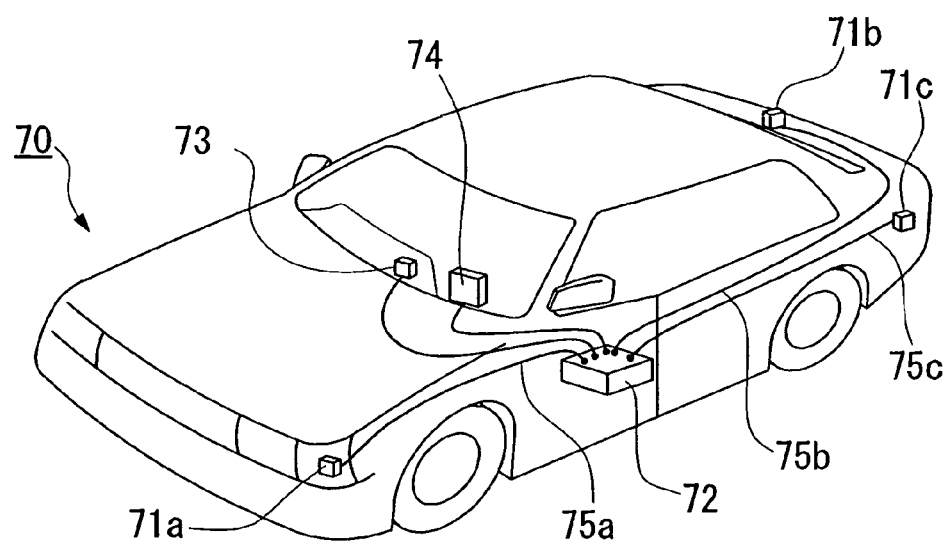
FIG. 9 is an isometric view for showing a general structure of an onboard camera system for an automobile in which an image capturing unit is used.

Next, an example for an onboard camera system 70 for an automobile in which the image capturing unit 1 is used is shown in FIG. 9. FIG. 9 is an isometric view for explaining an onboard camera system 70 for an automobile.

The onboard camera system 70 for an automobile comprises image capturing sections 71a, 71b, and 71c such that images which are captured by the image capturing sections 71a, 71b, and 71c can be displayed in a monitoring section 74 via a signal processing section 72 and a switching control section 73. The image capturing sections 71a, 71b, and 71c are connected to the signal processing section 72 via optical fibers 75a, 75b, and 75c respectively. The image capturing unit 1 has the same cross section in the optical axis direction as the cross section which is shown in FIG. 6C so as to be fixed in the image capturing sections 71a, 71b, and 71c.

As explained above, the image capturing device according to the present embodiment are provided with the image capturing units according to the first to fourth embodiments of the present invention. Therefore, it is possible to realize the same effect as the effect which are realized in the first to fourth embodiment.

According to the structures in the present embodiments, even if, for example, a light flux having a larger perspective angle than a scope of image which is supposed to be captured is incident, the light flux is disposed so as to have an appropriate interval from an inner diameter of the first electrode nearest to the first cover glass. Therefore, the light flux does not reach to the first electrode; thus, there occurs no flare nor no ghost light. Also, the light flux is disposed so as to have an appropriate interval from an inner diameter of the first electrode nearest to the second glass cover. Therefore, the light flux does not reach to the first electrode; thus, there occur no flare nor no ghost light.

Also, in the variable optical element, an area through which the light flux does not transmit is not excessively large. Therefore, it is not necessary to form a large variable optical element. As a result, it is possible to restrict the size of the image capturing device which is provided with the variable optical element; thus, it is possible to restrict an increase of cost.

According to the structure in the present embodiments, an area for a light flux which has the maximum perspective angle and transmits an interface between the first cover glass and the first liquid member is regulated. By doing this, it is possible compatibly to control an undesirable influence which is caused by a dust in the liquid members and restrict a deterioration of the image quality for an acceptable operation requirement.

As explained above, in the present embodiments, the interval between the first electrode and the light flux is regulated; thus, a flare light and a ghost light which are generated on inner wall surfaces on the variable optical element are restricted. Therefore, it is possible to restrict a deterioration of the image quality for an acceptable operation requirement.

According to the present embodiments, it is possible to restrict occurrence for the flare light and the ghost light by combining the variable optical element and the optical unit. Even if a light flux having a larger perspective angle than a scope of image which is supposed to be captured is incident, it is possible to dispose the light flux from the inner wall surface of the container with an appropriate interval as long as a certain necessary condition is satisfied. Therefore, the light flux does not reach to the inner wall surface of the container. As a result, the flare light nor the ghost light does not occur.

Also, in the variable optical element, an area through which the light flux does not transmit is not excessively large. Therefore, it is not necessary to form a large variable optical element. As a result, it is possible to restrict the size of the image capturing unit which is provided with the variable optical element. Also, it is possible to restrict an increase of a cost.

According to the present embodiments, it is possible to regulate an area for a light flux having the maximum perspective angle which is incident into the light-incident surface of the variable optical element in an appropriate size as long as a certain necessary condition is satisfied. Therefore, it does not occur that impurities such as a dust which is included in the first liquid member and the second liquid member in a manufacturing process may be observed in the captured image. As a result, the image quality is not deteriorated. Also, an interfacial area between the first liquid member and the second liquid member is not excessively large. Therefore, it is not difficult to control the electrocapillarity. As a result, the voltage is not applied so excessively high; thus, it is possible to realize a desirable accuracy for the shape.

According to the image capturing unit, a curvature for varying the interfacial shape can be set to be appropriate with reference to a length of the axial principal light between the position of the interface and the surface of the image capturing element. Therefore, the ghost light which is reflected on the interface is not focused in a small spot on the surface of the image capturing element. As a result, it is possible to reduce optical energy per an pixel on the image capturing element. Therefore, it is possible to restrict an undesirable influence for the image quality.

What is claimed is:

1. An image capturing unit comprising:
   a variable optical element;
   an optical unit which is disposed on a light-incident end of the variable optical element; and
   a light-flux limiting section, wherein
   the variable optical element includes a first liquid member, a second liquid member which does not mix in the first liquid member, and a container which contains the first liquid member and the second liquid member;
   an interfacial shape between the first liquid member and the second liquid member varies according to a voltage which is applied to the liquid members; and
   the light-influx limiting section satisfies a following condition (1);

$$0.1 < (\Phi - 2 \times h) < 20.0 \tag{1}$$

where $\Phi$ (mm) indicates a maximum diameter for an axial light-flux in the variable optical element and h (mm) indicates a highest position of the axial light-flux on the light-incident end of the variable optical element.

2. An image capturing unit according to claim 1 comprising:
   an image capturing element; and
   a power supplying section, wherein
   the power supplying section commonly serves for capturing an image and varying optical characteristics.

3. An image capturing unit according to claim 1 wherein a refractive index in the first liquid member is different from a refractive index in the second liquid member.

4. An image capturing unit comprising:
   a variable optical element; and
   an optical unit which is disposed on a light-incident end of the variable optical element, wherein
   the variable optical elements comprises a first liquid member, a second liquid member which does not mix in the first liquid member, a container which contains the first liquid member and the second liquid member, and an aperture member having aperture sections on both end in which diameters in the aperture sections are different;
   the aperture section having a small diameter in the aperture member is disposed near the light-incident end;
   an interfacial shape between the first liquid member and the second liquid member varies according to a voltage which is applied to the liquid members; and satisfies following conditions (2) and (3);

$$0.1 < (\Phi_1 - 2 \times h_1) < 20.0 \tag{2}$$

$$0.1 < (\Phi_2 - 2 \times h_2) < 20.0 \tag{3}$$

where $\Phi_1$ (mm) indicates a diameter for a small aperture section in the aperture member, $\Phi_2$ (mm) indicates a diameter for a large aperture section in the aperture member, $h_1$ (mm) indicates a highest position of the axial light-flux on the light-incident end of the variable optical element, and $h_2$ (mm) indicates a highest position of the axial light-flux on the interface between the first liquid member and the second liquid member.

5. An image capturing unit comprising:
   a variable optical element; and
   a light-flux limiting section, wherein
   the variable optical element includes a first liquid member, a second liquid member which does not mix in the first liquid member, and a container which contains the first liquid member and the second liquid member;
   an interfacial shape between the first liquid member and the second liquid member varies according to a voltage which is applied to the liquid members; and
   the light-influx limiting section satisfies a following condition (4)

$$0.5 < S < 20.0 \tag{4}$$

where S (mm$^2$) indicates an area for a light flux having a maximum perspective on the light-incident end of the variable optical element.

6. An image capturing unit according to claim 5 wherein:
   the light flux limiting section serves for a cover glass which forms the container; and
   the light-incident surface serves for the interface between the cover glass and the first liquid member.

7. An image capturing unit comprising:
   a variable optical element; and
   an image capturing element, wherein
   the variable optical element includes a first liquid member, a second liquid member which does not mix in the first liquid member, and a container which contains the first liquid member and the second liquid member;
   an interfacial shape between the first liquid member and the second liquid member varies according to a voltage which is applied to the liquid members; and
   an absolute value for $R_{12}$-d is in a range between 10% and 500% of a length d (mm); where $R_{12}$ indicates a diameter of a curvature of the interface, and d indicates a length for an optical path length of an axial principal light between the interface and a surface of the image capturing element.

8. An image capturing unit according to claim 7 wherein the image capturing element is disposed on a light-emitting end of the variable optical element.

9. An image capturing device which is provided with the image capturing unit of claim 1.

10. A mobile phone comprising:
    the image capturing unit of claim 1;
    a displaying section;

an inputting button section;
a voice inputting-outputting section; and
an antenna.

11. An information terminal comprising:
the image capturing unit of claim 1;
a displaying section; and
a keyboard.

12. An endoscope device comprising:
the image capturing unit of claim 1;
a light source;
a signal processing circuit; and
a power supply section.

* * * * *